(12) United States Patent
Lee et al.

(10) Patent No.: US 11,860,944 B2
(45) Date of Patent: Jan. 2, 2024

(54) STATE-AWARE INTERFACE (71) Applicant: International Business Machines Corporation, Armonk, NY (US)

(72) Inventors: Kristen Zelenka Lee, Austin, TX (US); Naga Manojkasyap Chilakamarthy Venkata, Austin, TX (US); Natalie Watkins, Austin, TX (US); Zachary A. Silverstein, Jacksonville, FL (US); Jayanth Krishnan, Mahopac, NY (US)

(73) Assignee: International Business Machines Corporation, Armonk, NY (US)

( * ) Notice: Subject to any disclaimer, the term of this patent is extended or adjusted under 35 U.S.C. 154(b) by 76 days.

(21) Appl. No.: 16/939,129

(22) Filed: Jul. 27, 2020

(65) Prior Publication Data

US 2022/0027415 A1 Jan. 27, 2022

(51) Int. Cl.
*G06F 16/9032* (2019.01)
*G06F 40/35* (2020.01)
*G06F 3/01* (2006.01)
*G06F 40/56* (2020.01)
*A61B 5/16* (2006.01)

(52) U.S. Cl.
CPC ........ *G06F 16/90332* (2019.01); *G06F 3/011* (2013.01); *G06F 40/35* (2020.01); *G06F 40/56* (2020.01); *A61B 5/165* (2013.01)

(58) Field of Classification Search
CPC .... G06F 16/90332; G06F 40/35; G06F 40/56; G06F 3/011; A61B 5/165
See application file for complete search history.

(56) References Cited

U.S. PATENT DOCUMENTS

| | | | |
|---|---|---|---|
| 10,276,188 B2 | 4/2019 | Feast | |
| 10,567,314 B1 | 2/2020 | Chang | |
| 2006/0241359 A1* | 10/2006 | Nagai | G16H 20/30 |
| | | | 600/301 |
| 2018/0101776 A1 | 4/2018 | Osotio | |
| 2018/0108353 A1 | 4/2018 | Gustafson | |
| 2018/0357286 A1 | 12/2018 | Wang | |
| 2019/0385711 A1 | 12/2019 | Shriberg | |
| 2021/0083996 A1* | 3/2021 | Moon | G06N 20/00 |
| 2021/0098110 A1* | 4/2021 | Periyasamy | A61B 5/0205 |
| 2021/0118547 A1* | 4/2021 | Morris | G16H 20/30 |

FOREIGN PATENT DOCUMENTS

| | | |
|---|---|---|
| IN | 102663046 A | 9/2012 |
| KR | 101613259 B1 | 4/2016 |
| WO | 2019246239 A1 | 12/2019 |

OTHER PUBLICATIONS

"Affordable Mental Health Access With Proven Results", Mental Health Chatbot, Printed May 18, 2020, 6 pages, <https://www.x2ai.com/>.

(Continued)

*Primary Examiner* — Sonia L Gay
(74) *Attorney, Agent, or Firm* — Brian M. Restauro (57) ABSTRACT

Embodiments of the present invention provide methods, computer program products, and systems determine a user state based on received information. Embodiments of the present invention can, in response to determining a user state reaching a threshold value, perform an ameliorative action.

14 Claims, 5 Drawing Sheets

(56) References Cited

OTHER PUBLICATIONS

"IBM Watson Health AI Healthcare Solutions", IBM, Printed May 18, 2020, 9 pages, <https://www.ibm.com/watson-health>.

"Past predictions—5 in 5", IBM Research, Printed May 18, 2020, 3 pages, <https://www.research.ibm.com/5-in-5/past-predictions/>.

"Watson IoT Platform IBM Watson IoT", Printed May 18, 2020, 10 pages, <https://www.ibm.com/internet-of-things/solutions/iot-platform/watson-iot-platform>.

Bogomolov et al., "Daily Stress Recognition from Mobile Phone Data, Weather Conditions and Individual Traits", MM'14, Nov. 3-7, 2014, Orlando, Florida, USA, Copyright 2014 ACM 978-1-4503-3063-3/14/11, <http://dx.doi.org/10.1145/2647868.2654933>.

Chaves et al., "How should my chatbot interact? A survey on human-chatbot interaction design", © 2018 Association for Computing Machinery, arXiv:1904.02743v1 [cs.HC] Apr. 4, 2019, 44 pages.

Fitzpatrick et al., "Delivering Cognitive Behavior Therapy to Young Adults With Symptoms of Depression and Anxiety Using a Fully Automated Conversational Agent (Woebot): A Randomized Controlled Trial", JMIR Mental Health 2017 | vol. 4 | iss. 2, 11 pages, <http://mental.jmir.org/2017/2/e19/>.

Ghandeharioun et al., "EMMA: An Emotion-Aware Wellbeing Chatbot,", 2019 8th International Conference on Affective Computing and Intelligent Interaction (ACII), @2019 IEEE, 7 pages.

Hakim et al., "A Dialogic Analysis of Compliment Strategies Employed by Replika Chatbot", Third International Conference of Arts, Language and Culture (ICALC 2018), Advances in Social Science, Education and Humanities Research (ASSEHR), vol. 279, 6 pages.

Oh et al., "A Chatbot for Psychiatric Counseling in Mental Healthcare Service Based on Emotional Dialogue Analysis and Sentence Generation", 2017 IEEE 18th International Conference on Mobile Data Management, DOI 10.1109/MDM.2017.64, © 2017 IEEE, 6 pages.

Dimitropoulos, Stav, "A chatbot pulled me out of a 'really dark place'", BBC News, Jan. 7, 2020, 14 pages, <https://www.bbc.com/news/business-50432574>.

Kuribayashi, Makoto, "How AI chatbot technology can help boost service", Dec. 13, 2018, 3 pages, <https://www.ibm.com/blogs/client-voices/ai-chatbot-boost-service/>.

\* cited by examiner

STATE-AWARE INTERFACE

BACKGROUND

The present invention relates in general to interactive interfaces and in particular to state-aware chatbot interfaces.

A chatbot typically refers to a software application used to conduct an on-line chat conversation via text or text-to-speech, in lieu of providing direct contact with a live human agent. Generally, chatbots are designed to simulate the way a human would behave as a conversational partner. Most chatbot chatbot systems typically require continuous tuning and testing.

In most scenarios, chatbots are typically used in dialog systems for various purposes including customer service, request routing, or for information gathering. While some chatbot applications use extensive word-classification processes, natural language processors, and sophisticated AI, others simply scan for general keywords and generate responses using common phrases obtained from an associated library or database. Most chatbots are accessed on-line via website popups, or through virtual assistants.

SUMMARY

Embodiments of the present invention provide methods, computer program products, and systems to for generating a chatbot that facilities discussion. In one embodiment of the present invention, a computer-implemented method is provided comprising: determining a user state based on received information; and in response to determining a user state reaching a threshold value, performing an ameliorative action.

DETAILED DESCRIPTION

Embodiments of the present invention recognize problems with chatbots. Specifically, embodiments of the present invention recognize that output generation (e.g., simulated conversation) is fixed and limited and particularly fail with an unsaved query. Embodiments of the present invention further recognize that a chatbot's efficiency depends on language processing and is limited because of irregularities, such as accents and mistakes that can create an important barrier for international and multi-cultural organizations. Furthermore, embodiments of the present invention recognize that chatbots are unable to deal with multiple questions at the same time and so conversation opportunities are limited and require a large amount of conversational data to train.

Embodiments of the present invention recognize that these problems can be exacerbated depending on an industry the chatbot is utilized. For example, where the industry is in healthcare, chatbots that do not remember a query, can be problematic. Accordingly, embodiments of the present invention provide solutions for remembering a query. In this manner, embodiments of the present invention improve chatbots by simulating conversations that are more realistic. For example, embodiments of the present invention provide functionality to existing chatbots by allowing chatbots to remember previous interactions as discussed in greater detail later in this Specification.

In this embodiment, a query can be a any previous input received by a chatbot. Inputs can include information previously disclosed information such as facts pertinent to the analysis, such as previous questions, brightness and optimism (e.g., probing for value and benefit), judgment (e.g., difficulties or risks associated with an action), emotions (e.g., hunches, feelings, intuition, self-esteem, love, confidence, moods, etc.), creativity (e.g., to explore possibilities, alternatives, and new ideas).

Inputs can further include user information collected from one or more Internet of Things devices (e.g., smart devices, wearable technology, etc.). For example, information can include location information, directional information or changes in directional information that includes a user collected from GPS sensors of a device associated with the user (e.g., to detect movement within an area or movement away from an area). In certain other embodiments, user information can include weather data specific to the user's location, and background information of the user.

Inputs can further include biometric information collected from wearable technology (e.g., heart rate, perspiration, sleep activity, strain, etc.). User information can include health information. For example, in instances a user can grant access to medical records (e.g., baseline biometric measurements, emotions, etc.). Where applicable, a user can provide personality assessment information to state-aware program 110.

User information can also access and receive social interaction information (e.g., social interaction via one or more social media platforms of the user). For example, embodiments of the present invention can access a user's relationships and interaction information (e.g., responses to media content). Finally, user information can include one or more user preferences collected from one or more user devices. For example, user information can include device profiles, goals, browsing history, games played by the user, etc. Examples of goals can include a target amount of time spent in social engagement, target destinations to visit, physical activity goals, time spent outside of a residence, etc.

Embodiments of the present invention provide mechanisms for a user to opt-in and opt-out of data collection (e.g., previous inputs and user information). Certain embodiments of the present invention can transmit notifications to a user each time data is collected and/or otherwise used.

Figure 1:
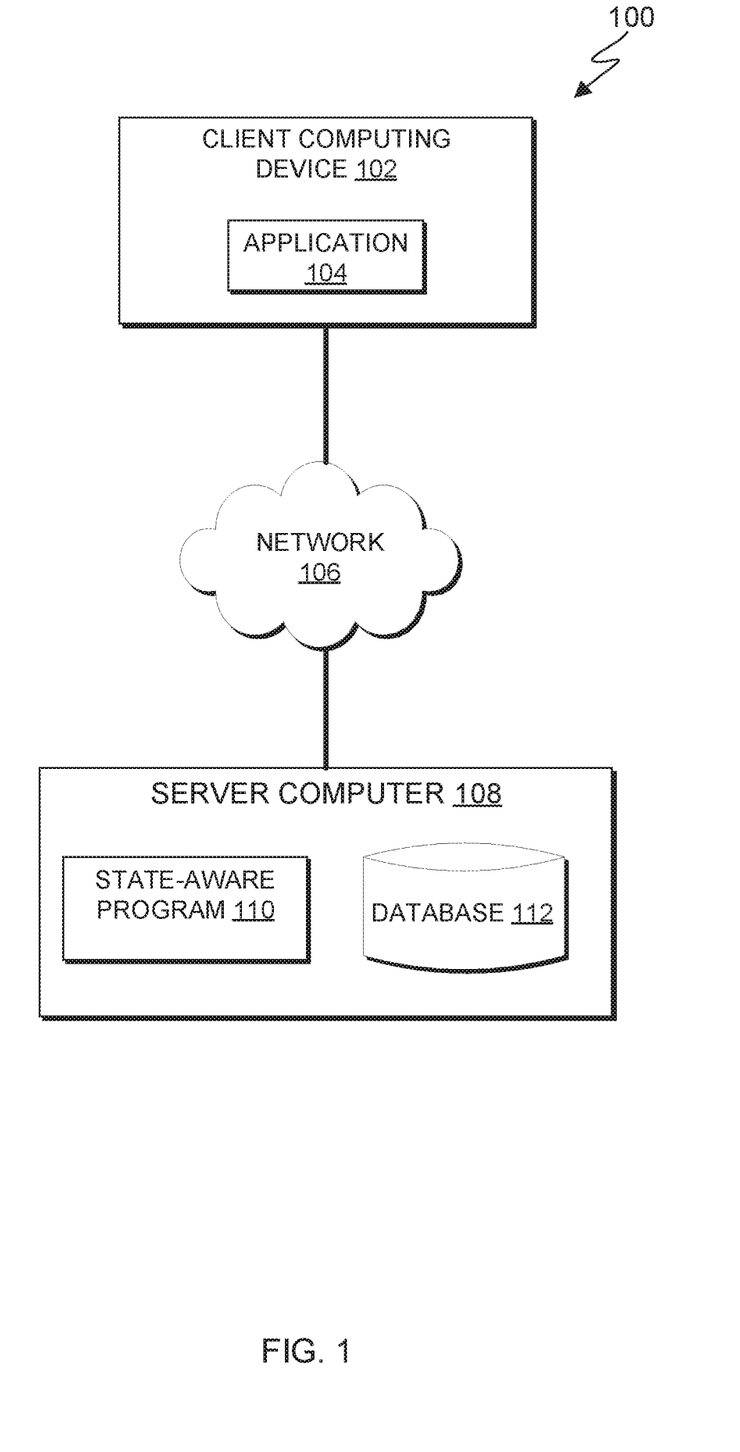
FIG. 1 is a functional block diagram illustrating a computing environment, in accordance with an embodiment of the present invention.

FIG. 1 is a functional block diagram illustrating a computing environment, generally designated, computing environment 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Computing environment 100 includes client computing device 102 and server computer 108, all interconnected over network 106. Client computing device 102 and server computer 108 can be a standalone computer device, a management server, a webserver, a mobile computing device, or any other electronic device or computing system capable of receiving, sending, and processing data. In other embodiments, client computing device 102 and server computer 108 can represent a server computing system utilizing multiple computer as a server system, such as in a cloud computing environment. In another embodiment, client computing device 102 and server computer 108 can be a laptop computer, a tablet computer, a netbook computer, a personal computer (PC), a desktop computer, a personal digital assistance (PDA), a smart phone, or any programmable electronic device capable of communicating with various components and other computing devices (not shown) within computing environment 100. In another embodiment, client computing device 102 and server computer 108 each represent a computing system utilizing clustered computers and components (e.g., database server computers, application server computers, etc.) that act as a single pool of seamless resources when accessed within computing environment 100. In some embodiments, client computing device 102 and server computer 108 are a single device. Client computing device 102 and server computer 108 may include internal and external hardware components capable of executing machine-readable program instructions, as depicted and described in further detail with respect to FIG. 5.

In this embodiment, client computing device includes application 104. Application 104 communicates with server computer 108 to access state-aware program 110 (e.g., using TCP/IP) to access user information and store and access inputs provided to state-aware program 110. Application 104 can further communicate with state-aware program 110 to transmit instructions perform ameliorative actions based on received inputs and predicted states of a user, as discussed in greater detail with regard to FIGS. 2-5.

Network 106 can be, for example, a telecommunications network, a local area network (LAN), a wide area network (WAN), such as the Internet, or a combination of the three, and can include wired, wireless, or fiber optic connections. Network 106 can include one or more wired and/or wireless networks that are capable of receiving and transmitting data, voice, and/or video signals, including multimedia signals that include voice, data, and video information. In general, network 106 can be any combination of connections and protocols that will support communications among client computing device 102 and server computer 108, and other computing devices (not shown) within computing environment 100.

Server computer 108 is a digital device that hosts state-aware program 110 and database 112. In this embodiment, state-aware program 110 resides on server computer 108 and can be implemented in a 5G infrastructure that interacts with cloud computing servers. In other embodiments, state-aware program 110 can have an instance of the program (not shown) stored locally on client computer device 102. In yet other embodiments, state-aware program 110 can be stored on any number or computing devices.

In this embodiment, state-aware program 110 receives user information, determines a user state and performs ameliorative actions to help the user based on previous interactions with state-aware program 110. In this embodiment, state-aware program 110 can include an activity module (not shown) that helps collect user information. State-aware program 110 improves upon existing chatbots by storing previous received inputs and accessing them (i.e., remembering previous inputs) during interactions with a user. In certain other embodiments, state-aware program 110 can incorporate a ground truth module that can verify context of a user state.

In this embodiment, state-aware program 110 determines a state of a user by determining a baseline state from previous user interactions. For example, state-aware program 110 can, with user permission, access user information to identify baseline measurements for biometric information, moods, emotions, etc. State-aware program 110 can then measure deviations from the baseline state by comparing baseline measurements to current received information. For example, state-aware program 110 can access a user's health information to determine a user's resting heart rate and then receive information that the user's heart rate is elevated (e.g., a normal resting heart rate of 70 beats per minute versus 130 beats per minute). State-aware program 110 can then identify a state based on measured deviations from the baseline. Continuing the example, state-aware program 110 can that the elevated heart rate can be associated with a state of a user (i.e., that elevated heart rate can be associated with anxiousness, stress, anger, etc.).

In this embodiment, state-aware program 110 determines a state of a user by observing user actions, grouping one or more user actions, assigning values to each observed action, and determining that a threshold value for the group is reached or exceeded. For example, state-aware program 110 can receive user information such as facial expression displayed by the user (e.g., frowning), biometric information (e.g., elevated heart rate and perspiration), and social media post (e.g., textual information). In this example, state-aware program 110 can group observed action within a specified time period. In this embodiment, a specified time period can include any period of time (e.g., seconds, minutes, hours, days, years, etc.).

Continuing the example above, state-aware program 110 can assign a point value for a facial expression, biometric information, and social media post. In this embodiment, a numeric scale is used, where higher numbers indicate a greater value than lower numbers which indicate a lesser value. For example, a value of five, is greater than a value of two. In this embodiment, a numeric scale can be a scale from zero to ten.

State-aware program 110 can then add the assigned values for the group (e.g., add the point values for facial expression, biometric information, and social media points), and determine that a threshold value for the group is reached or exceeded. In this embodiment, the threshold value can indicate whether or not state-aware program 110 performs an ameliorative action. For example, a threshold value of 6 (or 60%, where a scale from zero to 100% is used), could indicate that state-aware program 110 needs to perform an ameliorative action.

In response to state-aware program 110 determining that a threshold level for a user state is reached or exceeded, state-aware program 110 performs ameliorative actions. In this embodiment, an ameliorative action can include generating an interface that facilitates an interaction with a user. The generated interface can be generated as a preventative measure that can improve a user's state. For example, the generated interface can provide a suggestion to the user that, when completed, improves a user's state. An improvement can be measured as a change in a user's state. An improvement can verified by user input (e.g., a user indicating satisfaction). An improvement can be measured using facial recognition to identify a change from one state (e.g., sad, as indicated by a frown) to another state (e.g., happy, as indicated by a smile).

In certain embodiments, an ameliorative action can include one or more textual reminders, conversations, or alerts. Regardless of the communication medium, state-aware program 110 can select an appropriate tone when communicating with the user. For example, state-aware program 110 can select a gentle, insistent, encouraging, empowering, and/or empathetic tone when communicating with a user who is experiencing frustration. In these embodiments, state-aware program 110 can function in an iterative, self-learning manner to continually improve its selected responses and tone.

In this embodiment, database 112 functions as a repository for stored content. In this embodiment, content includes user profiles, device profiles and persona profiles. In some embodiments, database 112 can include ticket history or requests to participate in application and device improvement. Database 112 can reside on a cloud infrastructure and stores user generated information. In some embodiments, database 112 can function as a repository for one or more files containing user information. In this embodiment, database 112 is stored on server computer 108 however, database 112 can be stored on a combination of other computing devices (not shown) and/or one or more components of computing environment 100 (e.g., client computing device 102) and/or other databases that has given permission access to state-aware program 110.

In general, database 112 can be implemented using any non-volatile storage media known in the art. For example, database 112 can be implemented with a tape library, optical library, one or more independent hard disk drives, or multiple hard disk drives in a redundant array of independent disk (RAID). In this embodiment database 112 is stored on server computer 108.

Figure 2:
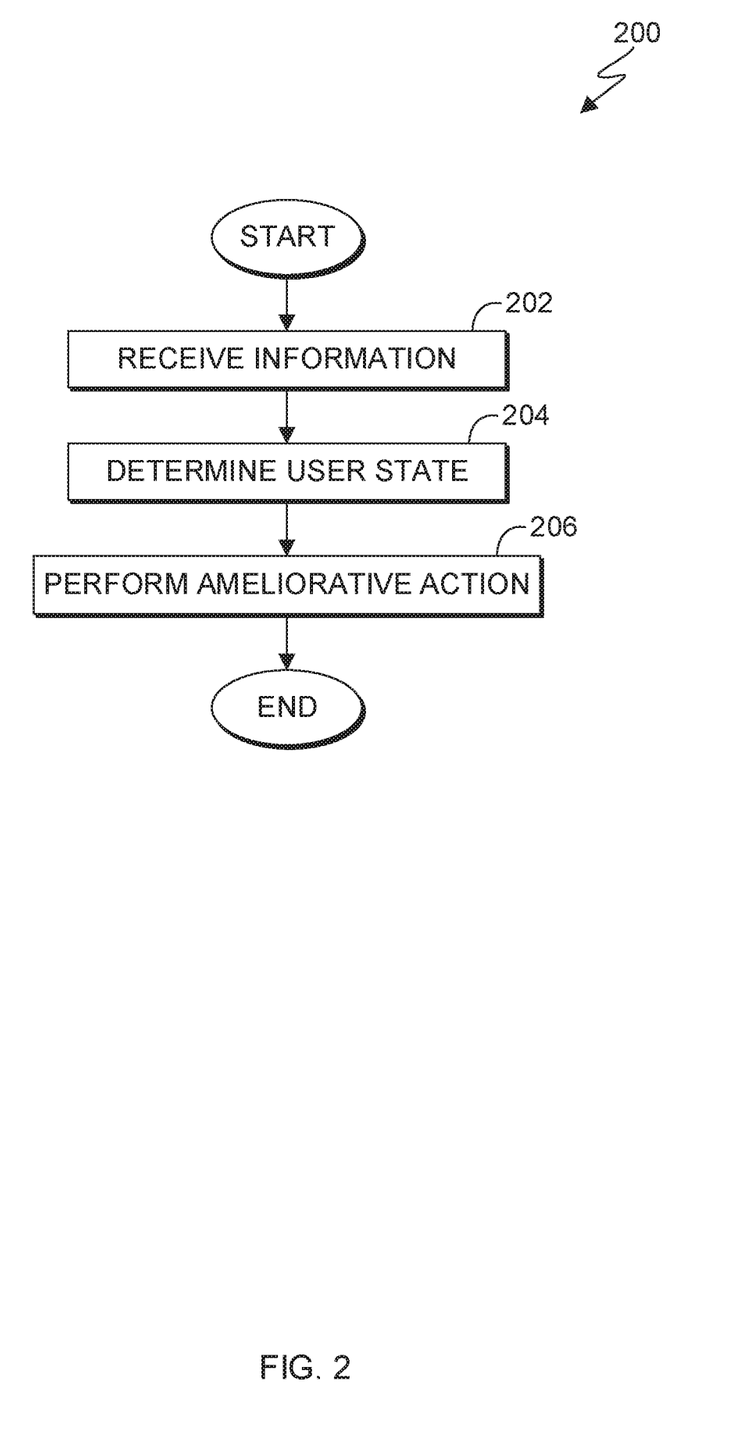
FIG. 2 is a flowchart depicting operational steps to perform an ameliorative action, in accordance with an embodiment of the present invention.

FIG. 2 is a flowchart 200 depicting operational steps to perform an ameliorative action, in accordance with an embodiment of the present invention.

In step 202, state-aware program 110 receives information. In this embodiment, state-aware program 110 receives information from application 104. In another embodiment, state-aware program 110 can receive information from one or more other components of computing environment 100.

As mentioned above, information can include inputs can include previous inputs, i.e., facts pertinent to the analysis, such as previous questions, brightness and optimism (e.g., probing for value and benefit), judgment (e.g., difficulties or risks associated with an action), emotions (e.g., hunches, feelings, intuition, self-esteem, love, confidence, moods, etc.), creativity (e.g., to explore possibilities, alternatives, and new ideas).

Inputs can further include user information collected from one or more Internet of Things devices (e.g., smart devices, wearable technology, etc.). For example, information can include location information, directional information or changes in directional information that includes a user collected from GPS sensors of a device associated with the user (e.g., to detect movement within an area or movement away from an area). Inputs can further include biometric information collected from wearable technology (e.g., heart rate, perspiration, sleep activity, strain, etc.). User information can include health information. For example, in instances a user can grant access to medical records. Where applicable, a user can provide personality assessment information to state-aware program 110.

User information can also access and receive social interaction information (e.g., social interaction via one or more social media platforms of the user). For example, embodiments of the present invention can access a user's relationships and interaction information (e.g., responses to media content). Finally, user information can include one or more user preferences collected from one or more user devices. For example, user information can include device profiles, goals, browsing history, games played by the user, etc.

In step 204, state-aware program 110 determines a user state. In this embodiment, state-aware program 110 determines a user state by generating a baseline of user activity and metrics, measuring deviations from a baseline state of the user, and identifying a state based on the measured deviations from the baseline as described in greater detail with regard to FIG. 3. For example, where a baseline measurements indicates that a user's "baseline state" indicates content, an observed frown that has been sustained over a period of time could indicate a deviation from the baseline.

Figure 4:
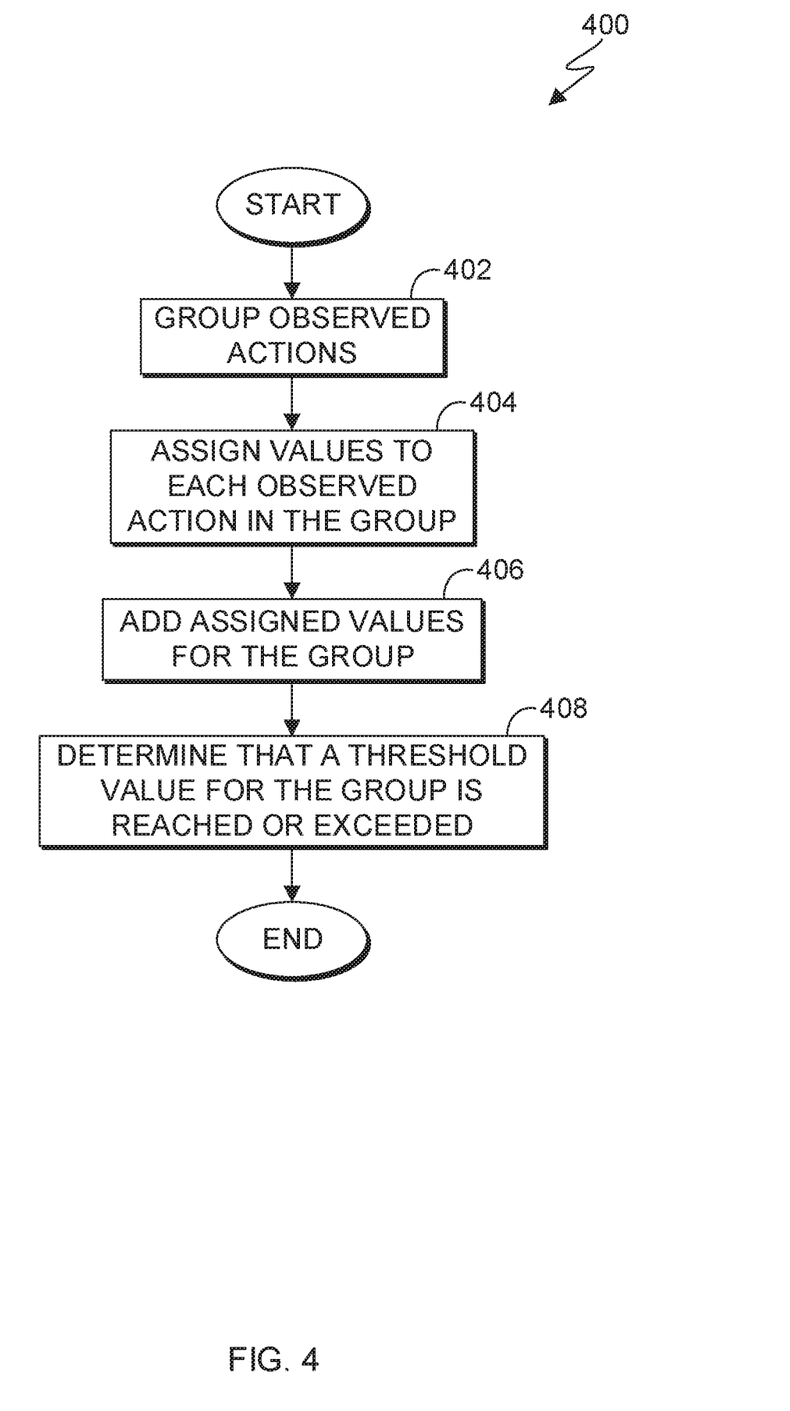
FIG. 4 a flowchart depicting operational steps to determine a user state, in accordance with an embodiment of the present invention.

In another embodiment, state-aware program 110 determines a user state by grouping observed actions, assigned point values to each observed action in the group and adding assigned values for the group, and determining that a threshold value for the group is reached or exceeded as discussed in greater detail with regard to FIG. 4. For example, state-aware program 110 can observe and record activity of a user within a pre-determined period (e.g., five minute time interval) and group each action, movement, expression, biometric information of a user, assign point values to each observed activity (e.g., action, movement, expression, biometric information, etc.), add the values, and determine whether the summed value reaches or exceeds a threshold value for a user state.

In step 206, state-aware program 110 performs an ameliorative action. In this embodiment, state-aware program 110 performs an ameliorative action by generating an interface that facilitates an interaction with a user and subsequently interact with a user. In this embodiment, state-aware program 110 can generate an interface that serves as a communication medium between state-aware program 110 and a user. State-aware program 110 can then initiate communication between the user and state-aware program 110.

In this embodiment, an ameliorative action can include an initiated interaction with a user. In this embodiment, an ameliorative action can be a textual, audio, or visual communication between state-aware program 110 and a user. For example, where text is the selected communication medium, state-aware program 110 can send text or email communication (e.g., reminder, conversation, suggestion, etc.)

State aware-program 110 can then select an appropriate tone when communicating with the user. For example, state-aware program 110 can select a gentle, insistent, encouraging, empowering, and/or empathetic tone when communicating with a user who is experiencing frustration. In these embodiments, state-aware program 110 can function in an iterative, self-learning manner to continually improve its selected responses and tone.

An ameliorative action can be presented as a communication to a user that is preventative in nature. Examples of preventative measures can be one or more actions that, when performed by the user, can improve a user's state. In this embodiment, state-aware program 110 measures an improvement can be measured as a change in a user's state (e.g., a return to a baseline state or a threshold value for a group of actions being scored as under a threshold value for intervention).

State-aware program 110 can provide a mechanism that can measure improvement. For example, state-aware program 110 can transmit a survey that solicits feedback from a user (e.g., a user indicating satisfaction). In certain embodiments, state-aware program 110 can measure improvement by measuring a combination of facial recognition, biometric, and behavior analysis to identify a change from one state (e.g., sad, as indicated by a frown) to another state (e.g., happy, as indicated by a smile).

State-aware program 110 can then store grouped actions, measured deviations, and known baselines for a user. State aware program 110 can then continually monitor the user and take ameliorative, preventative action based on deviations of current user behavior (as measured against known baseline behaviors and actions of the user). In this manner, state-aware program 110 improves chat bot systems by remembering previous interactions and taking appropriate action without the need for user input (i.e., user request to communicate).

Figure 3:
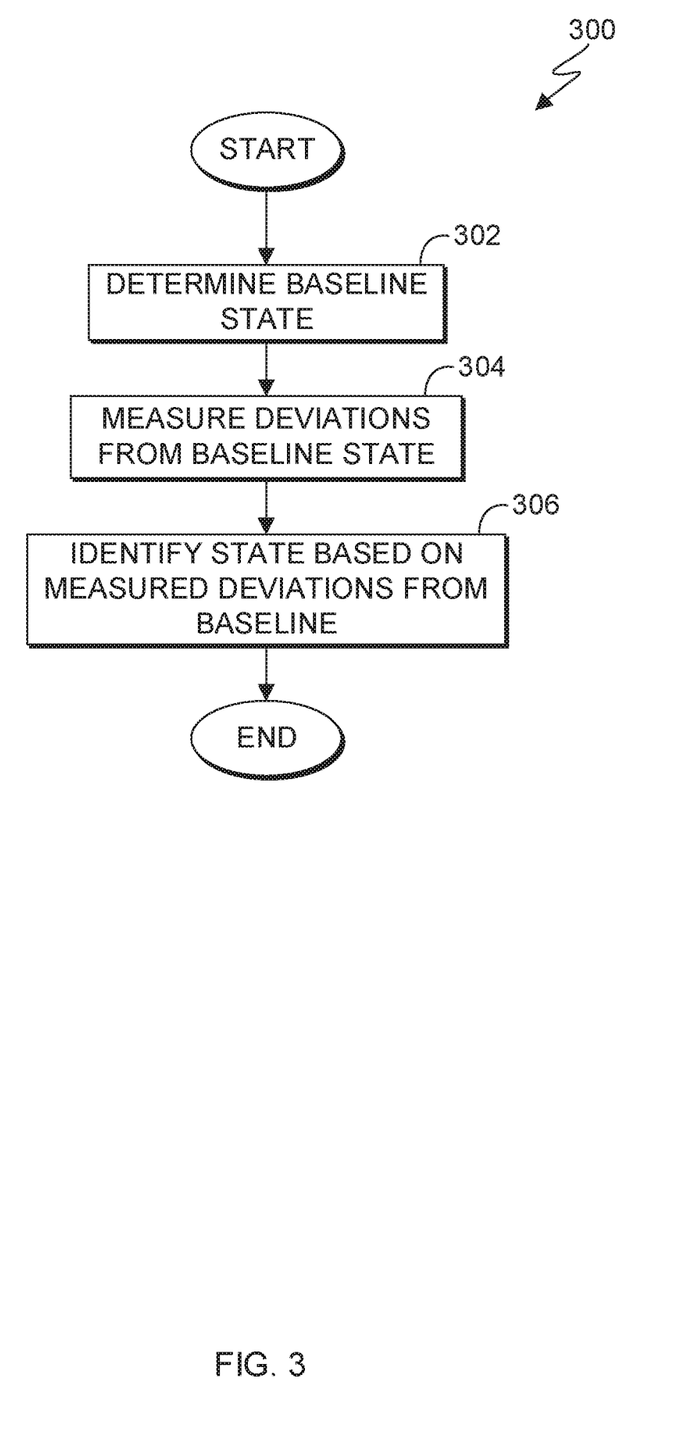
FIG. 3 is a flowchart depicting operational steps to determine a user state, in accordance with an embodiment of the present invention.

FIG. 3 is a flowchart 300 depicting operational steps to determine a user state, in accordance with an embodiment of the present invention.

In step 302, state-aware program 110 determines a baseline state of a user. In this embodiment, state aware program 110 can determine a baseline state of a user by accessing user information (as granted permission by the user). As stated above, user information can include biometric information collected from wearable technology (e.g., heart rate, perspiration, sleep activity, strain, etc.). User information can include health information. For example, in instances a user can grant access to medical records (e.g., baseline biometric measurements, emotions, etc.).

State-aware program 110 can access IoT devices of a user to determine a schedule followed by the user and set the schedule as a baseline measurement. For example, state-aware program 110 can access a user's calendar and determine that the user exercises every weekday morning before going to work, can determine a user's normal eating schedule (e.g., breakfast, lunch, dinner, etc.), and other patterns (e.g., breaks, walks, physical activity.). State aware program 110 can also access biometric information of a user and determine, for a given time period (e.g., a week), a user's baseline heart rate, activity level, sleep, etc.

In certain embodiments, state-aware program 110 can determine a baseline state of a user leveraging an artificial intelligence algorithm that helps determine and identify patterns from collected information. For example, in these embodiments, state-aware program 110 can collect information and transmit the collected information to be processed by one or more combinations of machine learning and artificial intelligence algorithms to identify patterned behavior of a user (e.g., user schedules, habits, moods, emotions, etc.).

In step 304, state-aware program 110 measures deviations from the baseline state of the user. In this embodiment, state-aware program 110 measures deviations from the baseline state of the user by comparing currently observed user information to established baseline states of a user. For example, where a baseline state of a user indicates that a user is content, collected information that shows a user's facial expression frowning indicates a deviation from the user's baseline state.

In step 306, state-aware program 110 identifies a state based on measured deviations from the baseline state of the user. In this embodiment, state-aware program 110 identifies a state based on a measured deviation from the baseline state of a user. For example, state-aware program 110 can access a user's baseline information (i.e., state) as being content and happy, with a resting heart rate of 60 beats per minute. The baseline information can also include that the user exercises regularly on weekday mornings. State-aware program 110 can then collect additional, current information of the user and identify that the user has not exercised in three days, and has an elevated resting heart rate. State-aware program 110 can additional leverage facial recognition technology to identify that the user's facial expression is consistent with frowning.

In scenarios where quantitative, biometric information is collected and observed, state-aware program can identify the increase in resting heart rate and decrease in amount of sleep the user is averaging. State-aware program 110 can verify the user has not exercised in three days using one or more IoT devices of the user to place the user inside the user's home and verify little physical movement within the user's home. Additionally, state-aware program 110 can access (with user permission), a user's social media platform to identify content shared by the user (e.g., textual posts that indicate a deviation from normal content shared by the user).

State-aware program 110 can then identify a state associated with the measured deviation. For example, state-aware program 110 can conclude that for a specific time period (e.g., a week) the little movement, content shared by the user, facial expressions, lack of sleep, increased resting heart rate, indicate a state of discontent.

In certain embodiments, state-aware program 110 can disregard deviations from a baseline state based on other contextual information. For example, where a user's baseline state indicates being happy and content and an observed action of frowning, state-aware program 110 can access other collected information to verify a measured deviation. Continuing the example, state-aware program 110 can identify that the user is viewing a device (e.g., a movie being displayed on a television) and determine that the user is reacting to a scene in the depicted content on the television. In these embodiments, state-aware program 110 can check other sources of collected information to support its conclusion of a deviation from a baseline state.

Accordingly, state-aware program 110 can then take appropriate ameliorative action as previously described in step 204 in flowchart 200.

FIG. 4 a flowchart 400 depicting operational steps to determine a user state, in accordance with an embodiment of the present invention.

In step 402, state-aware program 110 groups observed actions. In this embodiment, state-aware program 110 groups observed actions according to a pre-determined amount of time. For example, state-aware program 110 can group observed actions in regular, defined time periods (e.g., seconds, minutes, hours, days, weeks, months, years, etc.). In this embodiment, an action refers to a movement or series of movements performed by the user. An action can include facial expressions depicted by a user, tasks performed by the user, and interactions the user has with another person or object.

For example, state-aware program 110 can receive user information such as facial expression displayed by the user (e.g., frowning), biometric information (e.g., elevated heart rate and perspiration), and social media post (e.g., textual information). In this example, state-aware program 110 can group observed action within a specified time period. In this embodiment, a specified time period can include any period of time (e.g., seconds, minutes, hours, days, years, etc.).

In step 404, state-aware program 110 assigns values to each observed action in the group. In this embodiment, state-aware program 110 assigns values to each observed action in the group by assigning a numeric value of "1". Continuing the example above, state-aware program 110 can assign a point value for a facial expression, biometric information, and social media post.

In certain embodiments, state-aware program 110 can determine (i.e., derive) a context of the action and increase or decrease the assigned numeric value. For example, state-aware program 110 can determine that an interaction may have resulted in words that are traditionally associated with a negative mood (e.g., sadness, unhappiness, anger, etc.) but determine the words spoken had a different tone (e.g., said in jest) and therefore state-aware program 110 can modify the assigned numeric value.

In this embodiment, state-aware program 110 can generate subgroups of actions in the group of actions based on known associations (e.g., a matching of actions to known/stored actions of a user) of actions to moods of the user. For example, state-aware program 110 can record facial expression displayed by the user (e.g., frowning), biometric information (e.g., elevated heart rate and perspiration), and social media post (e.g., textual information), state-aware program 110 can group the facial expression and biometric information in a subgroup and group the social media post in another group based on associations of each of those actions. For example, state-aware program 110 can identify that the facial expression and biometric information are indicative of a negative mood while the social media post are indicative of a positive mood (e.g., happiness, contentment, etc.).

In step 406, state-aware program 110 adds assigned values for each respective action in the group. In this embodiment, state-aware program 110 adds assigned value for each respective action in either the group or subgroup of actions (e.g., add the point values for facial expression, biometric information, and social media points).

In step 408, state-aware program 110 determines that a threshold value for the group is reached or exceeded. In this embodiment, state-aware program 110 determines that a threshold value for the group is reached or exceeded by referencing the added assigned values and comparing the values to the threshold. In this embodiment, the threshold value can indicate whether state-aware program 110 performs an ameliorative action. For example, a threshold value of 6 (or 60%, where a scale from zero to 100% is used), could indicate that state-aware program 110 needs to perform an ameliorative action. In embodiments where there is a single score for the group of actions, state-aware program 110 can compare the single score to the threshold value to determine if the threshold value is reached or exceeded.

Figure 5:
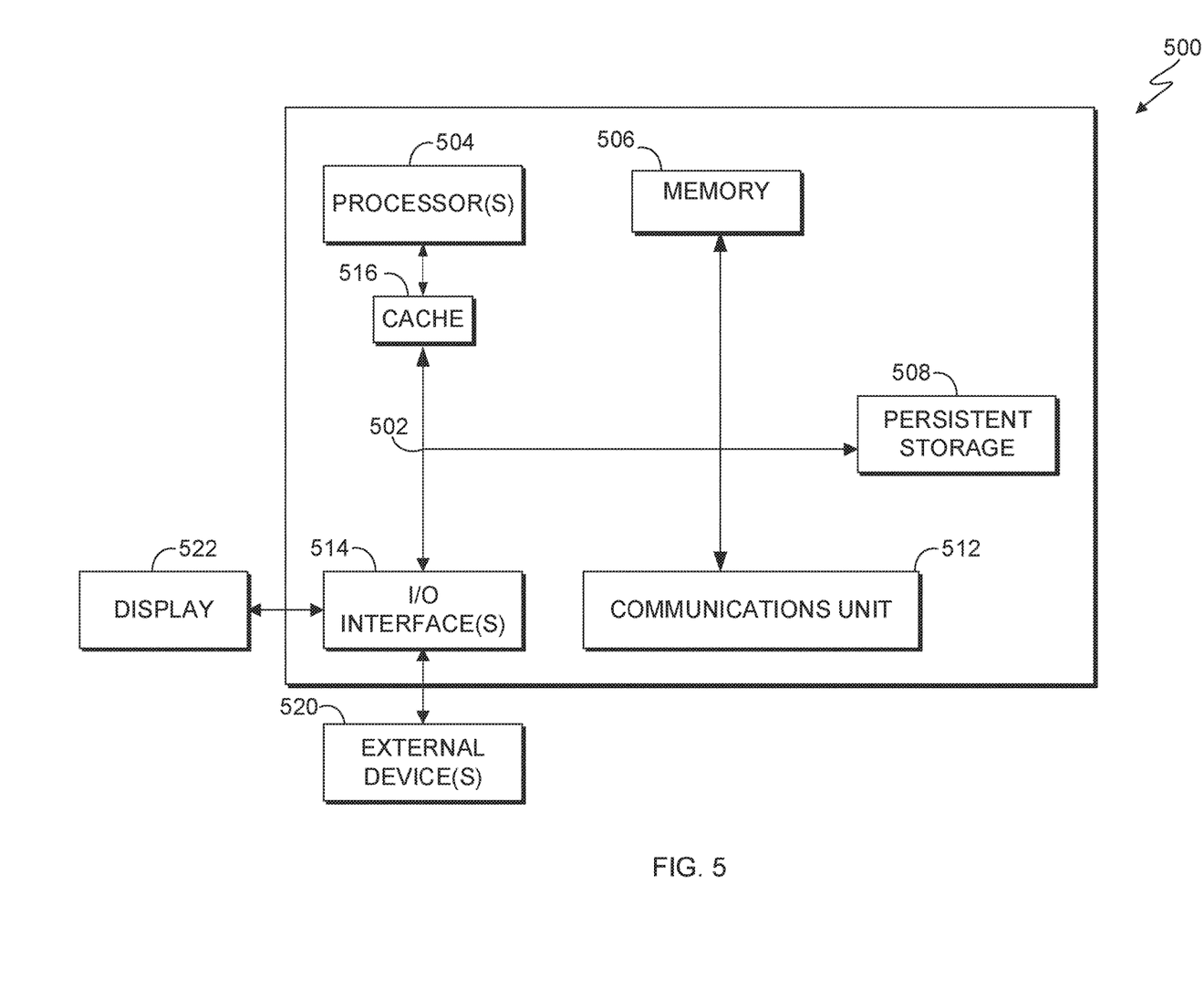
FIG. 5 depicts a block diagram of components of the computing systems of FIG. 1, in accordance with an embodiment of the present invention.

FIG. 5 depicts a block diagram of components of computing systems within computing environment 100 of FIG. 1, in accordance with an embodiment of the present invention. It should be appreciated that FIG. 5 provides only an illustration of one implementation and does not imply any limitations with regard to the environments in which different embodiments can be implemented. Many modifications to the depicted environment can be made.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Computer system 500 includes communications fabric 502, which provides communications between cache 516, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses or a crossbar switch.

Memory 506 and persistent storage 508 are computer readable storage media. In this embodiment, memory 506 includes random access memory (RAM). In general, memory 506 can include any suitable volatile or non-volatile computer readable storage media. Cache 516 is a fast memory that enhances the performance of computer processor(s) 504 by holding recently accessed data, and data near accessed data, from memory 506.

State-aware program 110 (not shown) may be stored in persistent storage 508 and in memory 506 for execution by one or more of the respective computer processors 504 via cache 516. In an embodiment, persistent storage 508 includes a magnetic hard disk drive. Alternatively, or in addition to a magnetic hard disk drive, persistent storage 508 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer readable storage medium that is also part of persistent storage 508.

Communications unit 510, in these examples, provides for communications with other data processing systems or devices. In these examples, communications unit 510 includes one or more network interface cards. Communications unit 510 may provide communications through the use of either or both physical and wireless communications links. State-aware program 110 may be downloaded to persistent storage 508 through communications unit 510.

I/O interface(s) 512 allows for input and output of data with other devices that may be connected to client computing device and/or server computer. For example, I/O interface 512 may provide a connection to external devices 518 such as a keyboard, keypad, a touch screen, and/or some other suitable input device. External devices 518 can also include portable computer readable storage media such as, for example, thumb drives, portable optical or magnetic disks, and memory cards. Software and data used to practice embodiments of the present invention, e.g., state-aware program 110, can be stored on such portable computer readable storage media and can be loaded onto persistent storage 508 via I/O interface(s) 512. I/O interface(s) 512 also connect to a display 520.

Display 520 provides a mechanism to display data to a user and may be, for example, a computer monitor.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
   determining a user state based on received information, wherein determining a user state comprises:
   grouping observed actions within a specified time period;
   assigning values to each observed action in the group based, at least in part, on context derived to respective observed actions,
   adding the assigned values to each observed action in the group,
   associating each observed action in the group to a state based on a matching of an observed action to a stored action associated with a known state,
   grouping one or more observed actions in the group into subgroups based on the matching, and
   determining whether a threshold value for observed actions in the group is reached or exceeded; and
   in response to determining a user state reaching a threshold value based on the threshold value for observed actions in the group, improving an automated response environment by generating a state aware interface that facilitates interactions with a user and recalls previous interactions with the user based on the determined user state.

2. The computer-implemented method of claim 1, wherein determining a user state comprises:
   determining a baseline state from received information;
   measuring deviations from the baseline state; and
   identifying a user state based on measured deviations.

3. The computer-implemented method of claim 1, wherein performing an ameliorative action comprises:
   generating a user interface that simulates conversation with a user;
   initiating communication with the user using the generated user interface; and
   storing the initiated communication with the user in a database.

4. The computer-implemented method of claim 3, further comprising:
   initiating the generated user interface based on the user state.

5. The computer-implemented method of claim 1, wherein an ameliorative action comprises: textual output that, when performed by the user, improves the user's state.

6. A computer program product comprising:
   one or more computer readable storage media and program instructions stored on the one or more computer readable storage media, the program instructions comprising:
   program instructions to determine a user state based on received information, wherein the program instructions to determine a user state comprise:
   program instructions to group observed actions within a specified time period;
   program instructions to assign values to each observed action in the group based, at least in part, on context derived to respective observed actions,
   program instructions to add the assigned values to each observed action in the group,
   program instructions to associate each observed action in the group to a state based on a matching of an observed action to a stored action associated with a known state,
   program instructions to group one or more observed actions in the group into subgroups based on the matching, and
   program instructions to determine whether a threshold value for observed actions in the group is reached or exceeded; and
   program instructions to, in response to determining a user state reaching a threshold value based on the threshold value for observed actions in the group, improve an automated response environment by generating a state aware interface that facilitates interactions with a user and recalls previous interactions with the user based on the determined user state.

7. The computer program product of claim 6, wherein the program instructions to determine a user state comprise:
   program instructions to determine a baseline state from received information;
   program instructions to measure deviations from the baseline state; and
   program instructions to identify a user state based on measured deviations.

8. The computer program product of claim 6, wherein the program instructions to perform an ameliorative action comprise:
   program instructions to generate a user interface that simulates conversation with a user;
   program instructions to initiate communication with the user using the generated user interface; and
   program instructions to store the initiated communication with the user in a database.

9. The computer program product of claim 8, wherein the program instructions stored on the one or more computer readable storage medium further comprise:
   program instructions to initiate the generated user interface based on the user state.

10. The computer program product of claim 6, wherein an ameliorative action comprises: textual output that, when performed by the user, improves the user's state.

11. A computer system comprising:
    one or more computer processors;
    one or more computer readable storage media; and
    program instructions stored on the one or more computer readable storage media for execution by at least one of the one or more computer processors, the program instructions comprising:
    program instructions to determine a user state based on received information, wherein the program instructions to determine a user state comprise:
    program instructions to group observed actions within a specified time period;
    program instructions to assign values to each observed action in the group based, at least in part, on context derived to respective observed actions,
    program instructions to add the assigned values to each observed action in the group,
    program instructions to associate each observed action in the group to a state based on a matching of an observed action to a stored action associated with a known state,
    program instructions to group one or more observed actions in the group into subgroups based on the matching, and
    program instructions to determine whether a threshold value for observed actions in the group is reached or exceeded; and
    program instructions to, in response to determining a user state reaching a threshold value based on the threshold value for observed actions in the group, improve an automated response environment by generating a state aware interface that facilitates interactions with a user and recalls previous interactions with the user based on the determined user state.

12. The computer system of claim 11, wherein the program instructions to determine a user state comprise:
program instructions to determine a baseline state from received information;
program instructions to measure deviations from the baseline state; and
program instructions to identify a user state based on measured deviations.

13. The computer system of claim 11, wherein the program instructions to perform an ameliorative action comprise:
program instructions to generate a user interface that simulates conversation with a user;
program instructions to initiate communication with the user using the generated user interface; and
program instructions to store the initiated communication with the user in a database.

14. The computer system of claim 11, wherein the program instructions stored on the one or more computer-readable storage medium further comprise:
program instructions to initiate the generated user interface based on the user state.

* * * * *